(12) United States Patent
Muller et al.

(10) Patent No.: US 7,459,466 B2
(45) Date of Patent: *Dec. 2, 2008

(54) SUBSTITUTED 2-(2,6-DIOXOPIPERIDIN-3-YL)-PHTHALIMIDES AND -1-OXOISOINDOLINES AND METHOD OF REDUCING TNFα LEVELS

(75) Inventors: George W. Muller, Bridgewater, NJ (US); David I. Stirling, Branchburg, NJ (US); Roger Shen-Chu Chen, Edison, NJ (US)

(73) Assignee: Celgene Corporation, Summit, NJ (US)

( * ) Notice: Subject to any disclaimer, the term of this patent is extended or adjusted under 35 U.S.C. 154(b) by 561 days.

This patent is subject to a terminal disclaimer.

(21) Appl. No.: 11/035,817

(22) Filed: Jan. 14, 2005

(65) Prior Publication Data

US 2005/0131024 A1    Jun. 16, 2005

Related U.S. Application Data

(60) Division of application No. 10/143,416, filed on May 10, 2002, now abandoned, which is a continuation of application No. 09/445,002, filed as application No. PCT/US98/10886 on May 28, 1998, now Pat. No. 6,395,754.

(60) Provisional application No. 60/048,278, filed on May 30, 1997.

(51) Int. Cl.
A61K 31/445    (2006.01)
C07D 401/04    (2006.01)

(52) U.S. Cl. ...................... 514/323; 546/201
(58) Field of Classification Search ................ 514/323; 546/201
See application file for complete search history.

(56) References Cited

U.S. PATENT DOCUMENTS

| | | | |
|---|---|---|---|
| 5,385,901 A | 1/1995 | Kaplan et al. | |
| 5,593,990 A | 1/1997 | D'Amato | |
| 5,629,327 A | 5/1997 | D'Amato | |
| 5,635,517 A | 6/1997 | Muller et al. | |
| 5,698,579 A | 12/1997 | Muller | |
| 5,712,291 A | 1/1998 | D'Amato | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,071,948 A | 6/2000 | D'Amato | |
| 6,228,879 B1 | 5/2001 | Green et al. | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,358,945 B1 * | 3/2002 | Breitfelder et al. | ....... 514/227.8 |
| 6,380,239 B1 | 4/2002 | Muller et al. | |
| 6,395,754 B1 | 5/2002 | Muller et al. | |
| 6,403,613 B1 * | 6/2002 | Man et al. | .................... 514/323 |
| 6,420,414 B1 | 7/2002 | D'Amato | |
| 6,458,810 B1 | 10/2002 | Muller et al. | |
| 6,469,045 B1 | 10/2002 | D'Amato | |
| 6,476,052 B1 * | 11/2002 | Muller et al. | ............... 514/323 |
| 6,518,298 B2 | 2/2003 | Green et al. | |
| 6,555,554 B2 | 4/2003 | Muller et al. | |
| 6,673,828 B1 | 1/2004 | Green et al. | |
| 6,762,195 B2 | 7/2004 | Muller et al. | |
| 6,977,268 B2 | 12/2005 | D'Amato | |
| 2001/0056114 A1 | 12/2001 | D'Amato | |
| 2002/0045643 A1 | 4/2002 | Muller et al. | |
| 2002/0052398 A1 | 5/2002 | D'Amato | |
| 2002/0054899 A1 | 5/2002 | D'Amato | |
| 2002/0161023 A1 | 10/2002 | D'Amato | |
| 2002/0173658 A1 | 11/2002 | Muller et al. | |
| 2002/0183360 A1 | 12/2002 | Muller et al. | |
| 2003/0028028 A1 | 2/2003 | Man et al. | |
| 2003/0045552 A1 | 3/2003 | Robarge | |
| 2003/0096841 A1 | 5/2003 | Robarge | |
| 2003/0139451 A1 * | 7/2003 | Shah et al. | .................. 514/323 |
| 2003/0144325 A1 | 7/2003 | Muller et al. | |
| 2003/0181428 A1 | 9/2003 | Green et al. | |
| 2003/0187024 A1 | 10/2003 | D'Amato | |
| 2003/0191098 A1 | 10/2003 | D'Amato | |
| 2003/0235909 A1 | 12/2003 | Hariri et al. | |
| 2004/0029832 A1 | 2/2004 | Zeldi | |
| 2004/0077685 A1 | 4/2004 | Figg et al. | |
| 2004/0077686 A1 | 4/2004 | Dannenberg et al. | |
| 2004/0087546 A1 | 5/2004 | Zeldis | |

(Continued)

FOREIGN PATENT DOCUMENTS

WO    WO 94/20085    9/1994

(Continued)

OTHER PUBLICATIONS

Schmahl et al. "The enantimers of the teratogenic . . . " CA 110:822 (1989).*

(Continued)

Primary Examiner—Celia Chang
(74) Attorney, Agent, or Firm—Jones Day

(57) ABSTRACT

Substituted 2-(2,6-dioxopiperidin-3-yl)-phthalimides and 1-oxo-2-(2,6-dioxopiperidin-3-yl)isoindolines reduce the levels of TNFα in a mammal. A typical embodiment is 1-oxo-2-(2,6-dioxo-3-methylpiperidin-3-yl)-4,5,6,7-tetrafluoroisoindoline.

9 Claims, No Drawings

U.S. PATENT DOCUMENTS

| | | |
|---|---|---|
| 2004/0091455 A1 | 5/2004 | Zeldis |
| 2004/0122052 A1 | 6/2004 | Muller et al. |
| 2004/0127545 A1 | 7/2004 | D'Amato et al. |
| 2004/0147558 A1 | 7/2004 | Treston et al. |
| 2004/0220144 A1 | 11/2004 | Zeldis |
| 2005/0096351 A1 | 5/2005 | Jaworsky et al. |
| 2005/0100529 A1 | 5/2005 | Zeldis |
| 2005/0143344 A1 | 6/2005 | Zeldis et al. |
| 2005/0143420 A1 | 6/2005 | Moutouh-de Parseval et al. |
| 2005/0203142 A1 | 9/2005 | Zeldis et al. |
| 2005/0214328 A1 | 9/2005 | Zeldis et al. |
| 2005/0222209 A1 | 10/2005 | Zeldis et al. |

FOREIGN PATENT DOCUMENTS

| | | |
|---|---|---|
| WO | WO 98/03502 | 1/1998 |
| WO | WO 98/19649 | 5/1998 |
| WO | WO 98/54170 | 12/1998 |
| WO | WO 01/43743 | 6/2001 |
| WO | WO 02/059106 | 8/2002 |
| WO | WO 02/064083 | 8/2002 |
| WO | WO 03/014315 | 2/2003 |
| WO | WO 03/086373 | 10/2003 |
| WO | WO 03/097052 | 11/2003 |
| WO | WO 2004/035064 | 4/2004 |
| WO | WO 2004/037199 | 5/2004 |
| WO | WO 2004/041190 | 5/2004 |
| WO | WO 2004/043377 | 5/2004 |
| WO | WO 2004/043464 | 5/2004 |
| WO | WO 2004/103274 | 12/2004 |
| WO | WO 2005/023192 | 3/2005 |
| WO | WO 2005/044178 | 5/2005 |
| WO | WO 2005/044259 | 5/2005 |
| WO | WO 2005/046318 | 5/2005 |
| WO | WO 2005/065455 | 7/2005 |
| WO | WO 2005/091991 | 10/2005 |
| WO | WO 2005/097125 | 10/2005 |
| WO | WO 2005/105088 | 11/2005 |
| WO | WO 2005/110408 | 11/2005 |
| WO | WO 2005/112928 | 12/2005 |

OTHER PUBLICATIONS

Benjamin et al. "A simple on-pot . . . " CA 2003:522224 (2003).*

U.S. Appl. No. 09/287,377, filed Apr. 7, 1999, D'Amato.

U.S. Appl. No. 09/545,654, filed Apr. 10, 2000, D'Amato (submit spec) (9516-116).

U.S. Appl. No. 10/003,461, filed Nov. 30, 2001, Treston et al. (submit spec) (9516-121).

U.S. Appl. No. 10/704,237, filed Nov. 6, 2003, Zeldis (submit spec) (9516-185).

Jonsson, N. Chemical Structure and Teratogenic Properties, Acta. Pharm. Succia, vol. 9, pp. 431-436 (1972).

Jonsson, N., Chemical Structure and Teratogenic Properties, Acta. Pharm. Succia, vol. 9 pp. 521-542 (1972).

Muller, George et al., Structural Modifications of Thalidomide Produce Analogs with Enhanced Tumor Necrosis Factor Inhibitory Activity, Journal of Medicinal Chemistry, vol. 39, No. 17, pp. 3238-3240 (1996).

Corral, L. et al., "Differential Cytokine Modulation and T Cell Activation by Two Distinct Classes of Thalidomide Analogues That are Potent Inhibitors of TNF-alpha 1", The Journal of Immunology, pp. 380-388 (1999).

Corral, L. et al., "Immunomodulation by Thalidomide and Thalidomide Analogues", Annals of the Rheumatic Diseases, vol. 58, Suppl. 1. pp. 1107-1113 (1999).

Corral, L. et al., "Selection of Novel Analogs of Thalidomide with Enhanced Tumor Necrosis Factor alpha Inhibitory Activity", Molecular Medicine, vol. 2, No. 4, pp. 506-515 (1996).

He, Weixuan et al., "Synthesis of Thalidomide Analogs and Their Biological Potential for Treatment of Graft Versus Host Disease (GVHD)", 206th American Chemical Society National Meeting, Med. Chem. Abst. 216 (1993).

Nishimura, K. et al., (S)-Form of alpha-Methyl-N (alpha)-phthalimidoglutarmide but not its (R)- Form, Enhanced Phorbol Ester-induced TNFalpha Production by Human Leukemia Cell HL-60; Implication of Optical Resolution of Thalilomidal Effect, Chem. Pharm. Bull. 42(5), 1157 (1994).

Koch, H., Thalidomide and congeners as Anti-inflammatory Agents, Progress in Medicinal Chemistry, vol. 22. pp. 166-214 (1985).

Miyachi, H. et al., Novel Biological Response Modifiers: Phthalimides with Tumor Necrosis Factor-alpha Production-Regulating Activity, J. Med. Chem., pp. 2858-2865 (1997).

Miyachi, H. et al., Tumor Necrosis Factor-alpha Production Enhancing Activity of Substituted 3'-Methylthalidomide: Influence of Substitutes at the hthaloyl Moiety on the Activity of Steroselectivity, Chem. Pharm. Bull., 46(7), pp. 1165-1168 (1998).

Muller, G. et al., Amino-Substituted Thalidomide Analogs: Potent Inhibitors of TNF-alpha Production, Bioorganic & Medicinal Chem. Letters 9, pp. 1625-1630 (1999).

Miyachi, H. et al., Enantio-Dependence of Inducer-Specific Bidirectional Regulation of Tumor Necrosis Factor (TNF)-alpha Production: Potent TNF-alpha Production Inhibitors, Biorg., Med. Chem. Letter 6(19) 2293 (1996).

Wnendt, S. et al., Enantioselective Inhibition of TNF-alpha Release by Thalidomide and Thalidomide-Analogues, Chirality 8, 390 (1996).

Muller, G. et al., Thlidomide Analogs and PDE4 Inhibition, Bioorganic & Medicinal Chemistry Letters 8, pp. 2669-2674 (1998).

Shannon, E. J., et al., Immunomodulatory Assays to Study Structure-Activity Relationships of Thalidomide, Immunopharmacology 35, pp. 203-212 (1997).

Takeuchi, Y. et al.—and (S)-3-Fluorothalidomides: Isosteric Analogues of Thalidomide, Organic Letters, vol. 1, No. 10, pp. 1571-1573 (1999).

Udagawa, T. et al., Thalidomide and Analogs, Antianglogenic Agents in Cancer Therapy, pp. 263-274.

* cited by examiner

SUBSTITUTED 2-(2,6-DIOXOPIPERIDIN-3-YL)-PHTHALIMIDES AND -1-OXOISOINDOLINES AND METHOD OF REDUCING TNFα LEVELS

This application is a divisional application of Ser. No. 10/143,416, filed May 10, 2002, now abandoned, which is a continuation of Ser. No. 09/445,002, filed Feb. 22, 2000, a 371 of PCT/US98/10886 filed May 28, 1998 and now U.S. Pat. No. 6,395,754, which claims benefit to U.S. Provisional Application No. 60/048,278 filed May 30, 1997, the disclosure of each of which is incorporated herein by reference in its entirety. This application claims the benefit of all of the applications.

The present invention relates to substituted 2-(2,6-dioxopiperidin-3-yl)-phthalimides and substituted 2-(2,6-dioxopiperidin-3-yl)-1-oxoisoindolines, the method of reducing levels of tumor necrosis factor α and treating inflammatory and autoimmune diseases in a mammal through the administration thereof, and to pharmaceutical compositions of such derivatives.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662-664 (1987) and Hinshaw et al., Circ. Shock 30, 279-292 (1990)}; cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712-714 (1989)}. Systemic infusion of recombinant TNFα also resulted in changes typically seen in ARDS {Ferrai-Baliviera et al., Arch. Surg. 124(12), 1400-1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516-518 (1986) and Johnson et al., Endocrinology 124(3), 1424-1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3-10 (1990)}. In Graft versus Host Reaction, increased serum TNFα levels have been associated with major complication following acute allogenic bone marrow transplants {Holler et al., Blood, 75(4), 1011-1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586-1591 (1989)}.

Macrophage-induced angiogenesis is known to be mediated by TNFα. Leibovich et al. {Nature, 329, 630-632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339-343, and Koch, Progress in Medicinal Chemistry, 22, 166-242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245-247 (1990)}. High levels of TNFα production (in the serum and in isolated macrophages) have been demonstrated in animal models of silica and asbestos induced fibrosis {Bissonnette et al., Inflammation 13(3), 329-339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36-42 (1990)}.

TNFα is also implicated in the inflammatory response which follows reperfusion, called reperfusion injury, and is a major cause of tissue damage after loss of blood flow {Vedder et al., PNAS 87, 2643-2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269-1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(1), 121-132 (1989)}.

TNFα blockage with monoclonal anti-TNFα antibodies has been shown to be beneficial in rheumatoid arthritis {Elliot et al., Int. J. Pharmac. 1995 17(2), 141-145} and Crohn's disease {von Dullemen et al., Gastroenterology, 1995 109(1), 129-135}.

Moreover, it now is known that TNFα is a potent activator of retrovirus replication including activation of HIV-1. {Duh et al., Proc. Nat. Acad. Sci. 86, 5974-5978 (1989); Poll et al., Proc. Nat. Acad. Sci. 87, 782-785 (1990); Monto et al., Blood 79, 2670 (1990); Clouse et al., J. Immunol. 142, 431-438 (1989); Poll et al., AIDS Res. Hum. Retrovirus, 191-197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad Sci*, 87, 782-784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., *PNAS* 86 2336-2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365-2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336-2340 (1989)}. TNFα in AIDS associated cachexia is suggested by elevated serum TNFα and high levels of spontaneous TNFα production in peripheral blood monocytes from patients {Wright et al., *J. Immunol.* 141(1), 99-104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227-29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762-66; Duh et al., *Proc. Natl. Acad. Sci.* 1989, 86, 5974-78; Bachelerie et al., *Nature* 1991, 350, 709-12; Boswas et al. *J. Acquired Immune Deficiency Syndrome* 1993, 6, 778-786; Suzuki et al., *Biochem. And Biophys. Res. Comm.* 1993, 193, 277-83; Suzuki et al., *Biochem. And Biophys. Res Comm.* 1992, 189, 1709-15; Suzuki et al., *Biochem. Mol. Bio. Int.* 1993, 31(4), 693-700; Shakhov et al., *Proc. Natl. Acad. Sci. USA* 1990, 171, 35-47; and Staal et al., *Proc. Natl. Acad. Sci. USA* 1990, 87, 9943-47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, inflammatory bowel disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470-474 (1985); WO 92/11383}.

DETAILED DESCRIPTION

The present invention is based on the discovery that certain classes of non-polypeptide compounds more fully described herein decrease the levels of TNFα.

In particular, the invention pertains to compounds of the formula:

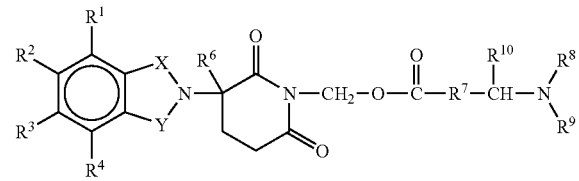

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$ and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —$(C_nH_{2n})$— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2XCH_2CH_2$— in which X is —O—, —S— or —NH—;
$R^{10}$ is hydrogen, alkyl of 1 to 8 carbon atoms, or phenyl; and
(b) the acid addition salts of said compounds which contain a nitrogen atom capable of being protonated.

A first preferred group of compounds are those of Formula I in which at least one of of $R^1$, $R^2$, $R^3$, $R^4$, and $R^6$ is other than hydrogen. Among these, a preferred group are those compounds in which each of $R^1$, $R^2$, $R^3$, and $R^4$, independently of the others, is halo, alkyl of 1 to 4 carbon atoms, or alkoxy of 1 to 4 carbon atoms; $R^6$ is hydrogen, methyl, ethyl, or propyl; each of $R^8$ and $R^9$ taken independently of the other is hydrogen or methyl; and $R^{10}$ is hydrogen. Of these compounds, a preferred subgroup are those compounds in which $R^7$ is m-phenylene or p-phenylene while a second preferred subgroup are those compounds in which $R^7$ —$(C_nH_{2n})$— in which n has a value of 0 to 4.

A further preferred group of compounds are those of Formula I in which one of $R^1$, $R^2$, $R^3$, and $R^4$ is —$NH_2$ and the remaining of $R^1$, $R^2$, $R^3$, and $R^4$ are hydrogen; $R^6$ is hydrogen, methyl, ethyl, or propyl; each of $R^8$ and $R^9$ taken independently of the other is hydrogen or methyl; and $R^{10}$ is hydrogen. Of these compounds, a first preferred subgroup are those compounds in which $R^7$ is m-phenylene or p-phenylene while a second preferred subgroup are those compounds in which $R^7$ —$(C_nH_{2n})$— in which n has a value of 0 to 4.

The term alkyl denotes a univalent saturated branched or straight hydrocarbon chain containing from 1 to 8 carbon atoms. Representative of such alkyl groups are methyl, ethyl, propyl, isopropyl, butyl, isobutyl, sec-butyl, and tert-butyl. Alkoxy refers to an alkyl group bound to the remainder of the molecule through an ethereal oxygen atom. Representative of such alkoxy groups are methoxy, ethoxy, propoxy, isopropoxy, butoxy, isobutoxy, sec-butoxy, and tert-butoxy. Preferably $R^1$, $R^2$, $R^3$, and $R^4$ are chloro, fluoro, methyl or methoxy.

The compounds of Formula I are used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, psoriasis, atopic dermatitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The compounds can be prepared through an initial reaction of formaldehyde with an intermediate of the formula:

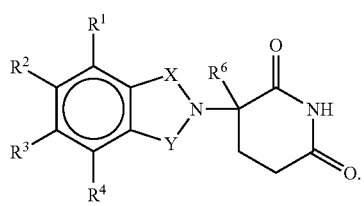

IIA in which X and Y are as defined above;
each of $R_1$, $R_2$, $R_3$, and $R_4$, independently of the others, is halo, alkyl of 1 to 4 carbon atoms, or alkoxy of 1 to 4 carbon atoms or (ii) one of $R_1$, $R_2$, $R_3$, and $R_4$ is nitro or protected amino and the remaining of $R_1$, $R_2$, $R_3$, and $R_4$ are hydrogen; and
$R_6$ is hydrogen, alkyl of 1 to 8 carbon atoms, benzo, chloro, or fluoro.

The resulting N-hydroxymethyl intermediate of Formula II then is coupled with a carboxylic acid derivative of Formula IV using methods which are known in general:

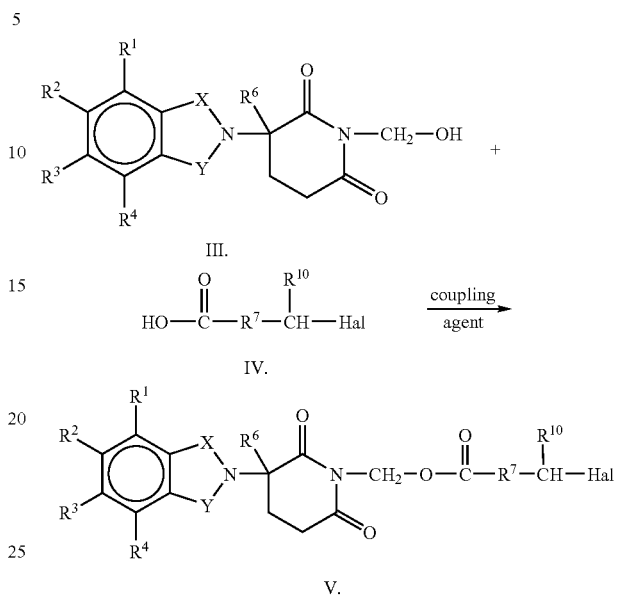

in which Hal is a reactive halogen such as chloro, bromo, or iodo.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups a re described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974, the disclosures of which are incorporated herein by reference.

An amino group can be protected as an amide utilizing an acyl group which is selectively removable under mild conditions, especially benzyloxycarbonyl, formyl, or a lower alkanoyl group which is branched in 1- or α position to the carbonyl group, particularly tertiary alkanoyl such as pivaloyl, a lower alkanoyl group which is substituted in the position a to the carbonyl group, as for example trifluoroacetyl.

Coupling agents include such reagents as dicyclohexylcarbodiimide and N,N'-carbonyldiimidazole.

Following coupling, compounds of Formula V can be aminated in a convention manner, as for example with an amine in the presence of sodium iodide.

Alternatively, a compound of Formula III is allowed to react with a protected aminocarboxylic acid of Formula IVA:

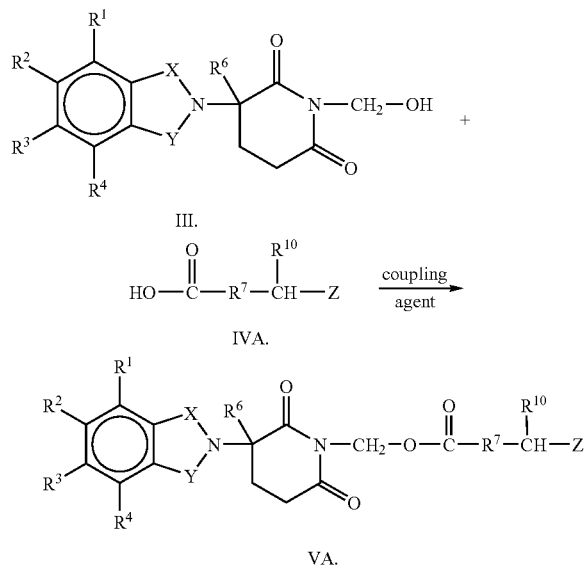

in which Z is a protected amino group.

Following this coupling, the amino protecting group Z is removed.

In the foregoing reactions when one of $R_1$, $R_2$, $R_3$, and $R_4$ is nitro, it can be converted to an amino group by catalytic hydrogenation. Alternatively, if one of $R_1$, $R_2$, $R_3$, and $R_4$ is protected amino, the protecting group can be cleaved to yield the corresponding compound in which one of $R_1$, $R_2$, $R_3$, and $R_4$ is amino.

In addition to serving as intermediates, certain other compound of Formula IIA are themselves biologically active in reducing levels of tumor necrosis factor α in a mammal. These compounds are those of the formula:

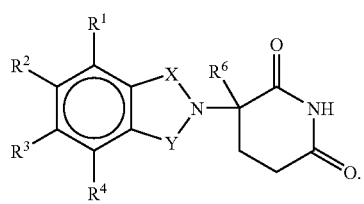

IIB in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen, alkyl of 1 to 8 carbon atoms, or CO—$R^7$—CH($R^{10}$)$NR^8R^9$ in which each of $R^7$, $R^8$, $R^9$, and $R^{10}$ is as herein defined; and
$R^6$ is alkyl of 1 to 8 carbon atoms, benzo, chloro, or fluoro.

Certain of the intermediates of Formula IIA are described in copending application Ser. Nos. 08/690,258, and 08/701,494, the disclosures of which are incorporated herein by reference. In addition, an alkyl o-bromomethylbenzoate which is appropriately substituted with $R^1$, $R^2$, $R^3$, and $R^4$ substituents is allowed to react with an α-$R^6$-substituted α-aminoglutarimide salt in the presence of an acid acceptor such as triethyl amine to yield compounds in which one of X and Y is C=O and the other is $CH_2$.

Compounds of Formula IIA in which X and Y are both C=O also can be prepared by allowing a phthalic anhydride which is appropriately substituted with $R^1$, $R^2$, $R^3$, and $R^4$ to react with an α-$R^6$-substituted α-aminoglutarimide salt in the presence of acetic acid and sodium acetate.

The α-$R^6$-substituted α-aminoglutarimide salt utilized in the foregoing reactions can be obtained by cyclizing an α-$R^6$-substituted glutamine in which the amino group is protected. The cyclization can be conducted for example with N,N'-carbonyldiimidazole in the presence of an acid acceptor such as dimethylaminopyridine. Upon completion of the reaction, the protecting group can be removed in an appropriate fashion. Solely by way of example, if the protecting group is the N-benzyloxycarbonyl group, it can be removed by catalytic hydrogenation.

The α-$R^6$-substituted glutamines in turn can be prepared by treating an α-$R^6$-substituted glutamic acid anhydride, in which the amino group is protected, with ammonia. Finally, the α-$R^6$-substituted glutamic acid anhydride can be obtained from the corresponding α-$R^6$-substituted glutamic acid with acetic anhydride.

The compounds of Formulas I and IIB possess a center of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, α-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

The present invention also pertains to the physiologically acceptable non-toxic acid addition salts of the compounds of Formulas I and IIB. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formulas I IIB associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

Oral dosage forms include tablets, capsules, dragees, and similar shaped, compressed pharmaceutical forms containing from 1 to 100 mg of drug per unit dosage. Isotonic saline solutions containing from 20 to 100 mg/mL can be used for parenteral administration which includes intramuscular, intrathecal, intravenous and intra-arterial routes of administration. Rectal administration can be effected through the use of suppositories formulated from conventional carriers such as cocoa butter.

Pharmaceutical compositions thus comprise one or more compounds of Formula I associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

EXAMPLE 1

N-Benzyloxycarbonyl-α-methyl-glutamic Acid

To a stirred solution of α-methyl-D,L-glutamic acid (10 g, 62 mmol) in 2 N sodium hydroxide (62 mL) at 0-5° C. was added benzyl chloroformate (12.7 g, 74.4 mmol) over 30 min. After the addition was complete the reaction mixture was stirred at room temperature for 3 hours. During this time the pH was maintained at 11 by addition of 2N sodium hydroxide (33 mL). The reaction mixture was then extracted with ether (60 mL). The aqueous layer was cooled in an ice bath and then acidified with 4N hydrochloric acid (34 mL) to pH=1. The resulting mixture was extracted with ethyl acetate (3×100 mL). The combined ethyl acetate extracts were washed with brine (60 mL) and dried (MgSO$_4$). The solvent was removed in vacuo to give 15.2 g (83%) of N-benzyloxycarbonyl-α-methylglutamic acid as an oil: $^1$H NMR (CDCl$_3$) δ 8.73(m, 5H), 5.77(b, 1H), 5.09(s, 2H), 2.45-2.27(m, 4H), 2.0(s, 3H).

In a similar fashion from α-ethyl-D,L-glutamic acid and α-propyl-D,L-glutamic acid, there is obtained N-benzyloxycarbonyl-α-ethylglutamic acid and N-benzyloxycarbonyl-α-propylglutamic acid, respectively.

EXAMPLE 2

N-Benzyloxycarbonyl-α-methyl-glutamic Anhydride

A stirred mixture of N-benzyloxycarbonyl-α-methylglutamic acid (15 g, 51 mmol) and acetic anhydride (65 mL) was heated at reflux under nitrogen for 30 min. The reaction mixture was cooled to room temperature and then concentrated in vacuo to afford N-benzylcarbonyl-α-methylglutamic anhydride as an oil (15.7 g) which can be used in next reaction without further purification: $^1$H NMR (CDCl$_3$) δ 7.44-7.26 (m, 5H), 5.32-5.30 (m, 2H), 5.11 (s, 1H), 2.69-2.61 (m, 2H), 2.40-2.30 (m, 2H), 1.68 (s, 3H).

In a similar fashion from N-benzyloxycarbonyl-α-ethylglutamic acid and N-benzyloxycarbonyl-α-propylglutamic acid, there is obtained N-benzylcarbonyl-α-ethylglutamic anhydride and N-benzylcarbonyl-α-propylglutamic anhydride, respectively.

EXAMPLE 3

N-Benzyloxycarbonyl-α-methylisoglutamine

A stirred solution of N-benzylcarbonyl-α-methylglutamic anhydride (14.2 g, 51.5 mmol) in methylene chloride (100 mL) was cooled in an ice bath. Gaseous ammonia was bubbled into the cooled solution for 2 hours. The reaction mixture was stirred at room temperature for 17 hours and then extracted with water (2×50 mL). The combined aqueous extracts were cooled in an ice bath and acidified with 4N hydrochloric acid (32 mL) to pH 1. The resulting mixture was extracted with ethyl acetate (3×80 mL). The combined ethyl acetate extracts were washed with brine (60 mL) and then dried (MgSO$_4$). The solvent was removed in vacuo to give 11.5 g of N-benzyloxycarbonyl-α-amino-α-methylisoglutamine: $^1$H NMR (CDCl$_3$/DMSO) δ 7.35 (m, 5H), 7.01 (s, 1H), 6.87 (s, 1H), 6.29 (s, 1H), 5.04 (s, 2H), 2.24-1.88 (m, 4H), 1.53 (s, 3H).

In a similar fashion from N-benzylcarbonyl-α-ethylglutamic anhydride and N-benzylcarbonyl-α-propylglutamic anhydride there is obtained N-benzyloxycarbonyl-α-amino- α-ethylisoglutamine and N-benzyloxycarbonyl-α-amino-α-propylisoglutamine, respectively.

EXAMPLE 4

N-Benzyloxycarbonyl-α-amino-α-methylglutarimide

A stirred mixture of N-benzyloxycarbonyl-α-methylisoglutamine (4.60 g, 15.6 mmol), 1,1'-carbonyldiimidazole (2.80 g, 17.1 mmol), and 4-dimethylaminopyridine (0.05 g) in tetrahydrofuran (50 mL) was heated to reflux under nitrogen for 17 hours. The reaction mixture was then concentrated in vacuo to an oil. The oil was slurried in water (50 mL) for 1 hour. The resulting suspension was filtered and the solid washed with water and air dried to afford 3.8 g of the crude product as a white solid. The crude product was purified by flash chromatography (methylene chloride:ethyl acetate 8:2) to afford 2.3 g (50%) of N-benzyloxycarbonyl-α-amino-α-methylglutarimide as a white solid: mp 150.5-152.5° C.; $^1$H NMR (CDCl$_3$) δ 8.21 (s, 1H), 7.34 (s, 5H), 5.59 (s, 1H), 5.08 (s, 2H), 2.74-2.57 (m, 3H), 2.28-2.25 (m, 1H), 1.54 (s, 3H); $^{13}$C NMR (CDCl$_3$) δ 174.06, 171.56, 154.68, 135.88, 128.06, 127.69, 127.65, 66.15, 54.79, 29.14, 28.70, 21.98; HPLC: Waters Nova-Pak C18 column, 4 micron, 3.9×150 mm, 1 mL/min, 240 nm, 20/80 CH$_3$CN/0.1% H$_3$PO$_4$(aq), 7.56 min (100%); Anal. Calcd For C$_{14}$H$_{16}$N$_2$O$_4$: C, 60.86; H, 5.84; N, 10.14. Found: C, 60.88; H, 5.72; N, 10.07.

In a similar fashion from N-benzyloxycarbonyl-α-amino-α-ethylisoglutamine and N-benzyloxycarbonyl-α-amino-α-propylisoglutamine there is obtained N-benzyloxycarbonyl-α-amino-α-ethylglutarimide and N-benzyloxycarbonyl-α-amino-α-propylglutarimide, respectively.

EXAMPLE 5

α-Amino-α-methylglutarimide Hydrochloride

N-Benzyloxycarbonyl-α-amino-α-methylglutarimide (2.3 g, 8.3 mmol) was dissolved in ethanol (200 mL) with gentle heat and the resulting solution allowed to cool to room temperature. To this solution was added 4N hydrochloric acid (3 mL) followed by 10% Pd/C (0.4 g). The mixture was hydrogenated in a Parr apparatus under 50 psi of hydrogen for 3 hours. To the mixture was added water (50 mL) to dissolve the product. This mixture was filtered through a Celite pad which was washed with water (50 mL). The filtrate was concentrated in vacuo to afford a solid residue. The solid was slurried in ethanol (20 mL) for 30 min. The slurry was filtered to afford 1.38 g (93%) of a-amino-α-methylglutarimide hydrochloride as a white solid: $^1$H NMR (DMSO-d$_6$) δ 11.25 (s, 1H), 8.92 (s, 3H), 2.84-2.51 (m, 2H), 2.35-2.09 (m, 2H), 1.53 (s, 3H); HPLC, Waters Nova-Pak C$_{18}$ column, 4 micron, 1 mL/min, 240 nm, 20/80 CH$_3$CN/0.1% H$_3$PO$_4$(aq), 1.03 min (94.6%).

In a similar fashion from N-benzyloxycarbonyl-α-amino-α-ethylglutarimide and N-benzyloxycarbonyl-α-amino-α-propylglutarimide there is obtained α-amino-α-ethylglutarimide hydrochloride and α-amino-α-propylglutarimide hydrochloride, respectively.

EXAMPLE 6

3-(3-Nitrophthalimido)-3-methylpiperidine-2,6-dione

A stirred mixture of α-amino-α-methylglutarimide hydrochloride (1.2 g, 6.7 mmol), 3-nitrophthalic anhydride (1.3 g, 6.7 mmol), and sodium acetate (0.6 g, 7.4 mmol) in acetic acid (30 mL) was heated to reflux under nitrogen for 6 hours. The mixture then was cooled and concentrated in vacuo. The resulting solid was slurried in water (30 mL) and methylene chloride (30 mL) for 30 min. The suspension was filtered, the solid was washed with methylene chloride, and dried in vacuo (60° C., <1 mm) to afford 1.44 g (68%) of 3-(3-nitrophthalimido)-3-methylpiperidine-2,6-dione as a off-white solid: mp 265-266.5° C.; $^1$H NMR (DMSO-d$_6$) δ 11.05 (s, 1H), 8.31 (dd, J=1.1 and 7.9 Hz, 1H), 8.16-8.03 (m, 2H), 2.67-2.49 (m, 3H), 2.08-2.02 (m, 1H), 1.88 (s, 3H); $^{13}$C NMR (DMSO-d$_6$) δ 172.20, 171.71, 165.89, 163.30, 144.19, 136.43, 133.04, 128.49, 126.77, 122.25, 59.22, 28.87, 28.49, 21.04; HPLC, Water Nova-Pak/C$_{18}$ is column, 4 micron, 1 mL/min, 240 nm, 20/80 CH$_3$CN/0.1% H$_3$PO$_4$(aq), 7.38 min(98%). Anal. Calcd For C$_{14}$H$_{11}$N$_3$O$_6$: C, 53.00; H, 3.49; N, 13.24. Found: C, 52.77; H, 3.29; N, 13.00.

In a similar fashion from α-amino-α-ethylglutarimide hydrochloride and α-amino-α-propylglutarimide hydrochloride there is obtained 3-(3-nitrophthalimido)-3-ethylpiperidine-2,6-dione and 3-(3-nitrophthalimido)-3-propylpiperidine-2,6-dione, respectively.

EXAMPLE 7

3-(3-Aminophthalimido)-3-methyl-piperidine-2,6-dione 3-(3-Nitrophthalimido)-3-methylpiperidine-2,6-dione (0.5 g, 1.57 mmol) was dissolved in acetone (250 mL) with gentle heat and then cooled to room temperature. To this solution was added 10% Pd/C (0.1 g) under nitrogen. The mixture was hydrogenated in a Parr apparatus at 50 psi of hydrogen for 4 hours. The mixture then was filtered through Celite and the pad washed with acetone (50 mL). The filtrate was concentrated in vacuo to yield a yellow solid. The solid was slurried in ethyl acetate (10 mL) for 30 minutes. The slurry then was filtered and dried (60° C., <1 mm) to afford 0.37 g (82%) of 3-(3-aminophthalimido)-3-methylpiperidine-2,6-dione as a yellow solid: mp 268-269° C.; $^1$H NMR (DMSO-d$_6$) δ 10.98 (s, 1H), 7.44 (dd, J=7.1 and 7.3 Hz, 1H), 6.99 (d, J=8.4 Hz, 1H), 6.94 (d, J=6.9 Hz, 1H), 6.52 (s, 2H), 2.71-2.47 (m, 3H), 2.08-1.99 (m, 1H), 1.87 (s, 3H); $^{13}$C NMR (DMSO-d$_6$) δ 172.48, 172.18, 169.51, 168.06, 146.55, 135.38, 131.80, 121.51, 110.56, 108.30, 58.29, 29.25, 28.63, 21.00; HPLC, Water Nova-Pak/C$_{18}$ column, 4 micron, 1 mL/min, 240 nm, 20/80 CH$_3$CN/0.1% H$_3$PO$_4$(aq), 5.62 min (99.18%). Anal. Calcd For C$_{14}$H$_{13}$N$_3$O$_4$: C, 58.53; H, 4.56; N, 14.63. Found: C, 58.60; H, 4.41; N, 14.36.

In a similar fashion from 3-(3-nitrophthalimido)-3-ethylpiperidine-2,6-dione and 3-(3-nitrophthalimido)-3-propylpiperidine-2,6-dione there is obtained 3-(3-amino-phthalimido)-3-ethylpiperidine-2,6-dione and 3-(3-aminophthalimido)-3-propyl-piperidine-2,6-dione, respectively.

EXAMPLE 8

Methyl 2-bromomethyl-3-nitrobenzoate

A stirred mixture of methyl 2-methyl-3-nitrobenzoate (17.6 g, 87.1 mmol) and N-bromosuccinimide (18.9 g, 105 mmol) in carbon tetrachloride (243 mL) was heated under gentle reflux with a 100 W light bulb situated 2 cm away shining on the reaction mixture overnight. After 18 hours, the reaction mixture was cooled to room temperature and filtered. The filtrate was washed with water (2×120 mL), brine (120 mL), and dried (MgSO$_4$). The solvent was removed in vacuo to give a yellow solid. The product was purified by flash chromatography (hexane:ethyl acetate 8:2) to give 22 g (93%) of methyl 2-bromomethyl-3-nitrobenzoate as a yellow solid: mp 69-72° C.; $^1$H NMR (CDCl$_3$) δ 8.13-8.09 (dd, J=1.36 and 7.86 Hz, 1H), 7.98-7.93 (dd, J=1.32 and 8.13 Hz, 1H), 7.57-7.51 (t, J=7.97 Hz, 1H), 5.16 (s, 2H), 4.0 (s, 3H); $^{13}$C NMR (CDCl$_3$) δ 65.84, 150.56, 134.68, 132.64, 132.36, 129.09, 53.05, 22.70; HPLC: Waters Nova-Pak C$_{18}$ column, 4 micron, 1 mL/min, 240 nm, 40/60 CH$_3$CN/0.1% H$_3$PO$_4$(aq), 8.2 min 99%. Anal. Calcd for C$_9$H$_8$NO$_4$Br: C, 39.44; H, 2.94; N, 5.11, Br, 29.15. Found: C, 39.51; H, 2.79; N, 5.02; Br, 29.32.

EXAMPLE 9

3-(1-Oxo-4-nitroisoindolin-1-yl)-3-methylpiperidine-2,6-dione

To a stirred mixture of α-amino-α-methylglutarimide hydrochloride (2.5 g, 14.0 mmol) and methyl 2-bromomethyl-3-nitrobenzoate(3.87 g, 14.0 mmol in dimethylformamide (40 mL) was added triethylamine (3.14 g, 30.8 mmol). The resulting mixture was heated to reflux under nitrogen for 6 hours. The mixture was cooled and then concentrated in vacuo. The resulting solid was slurried in water (50 mL) and CH$_2$Cl$_2$ for 30 min. The slurry was filtered, the solid washed with methylene chloride, and dried in vacuo (60° C., <1 mm) to afford 2.68 g (63%) of 3-(1-oxo-4-nitroisoindolin-1-yl)-3-methylpiperidine-2,6-dione as a off-white solid: mp 233-235° C.; $^1$H NMR (DMSO-d$_6$) δ 10.95 (s, 1H), 8.49-8.46 (d, J=8.15 Hz, 1H), 8.13-8.09 (d, J=7.43 Hz, 1H), 7.86-7.79 (t, J=7.83 Hz, 1H), 5.22-5.0 (dd, J=19.35 and 34.6 Hz, 2H), 2.77-2.49 (m, 3H), 2.0-1.94 (m, 1H), 1.74 (S, 3H); $^{13}$C NMR (DMSO-d$_6$) δ 173.07, 172.27, 164.95, 143.15, 137.36, 135.19, 130.11, 129.32, 126.93, 57.57, 48.69, 28.9, 27.66, 20.6; HPLC, Waters Nova-Pak C$_{18}$ column, 4 micron, 1 mL/min, 240 nm, 20/80 CH$_3$CN/0.1% H$_3$PO$_4$(aq), 4.54 min 99.6%. Anal. Calcd for C$_{14}$H$_{13}$N$_3$O$_5$: C, 55.45; H, 4.32; N, 13.86. Found: C, 52.16; H, 4.59; N, 12.47.

By substituting equivalent amounts of α-amino-α-ethylglutarimide hydrochloride and α-amino-α-propylglutarimide hydrochloride for α-amino-α-methylglutarimide hydrochloride, there is obtained respectively 3-(1-oxo-4-nitroisoindolin-1-yl)-3-ethylpiperidine-2,6-dione and 3-(1-oxo-4-nitroisoindolin-1-yl)-3-propylpiperidine-2,6-dione.

EXAMPLE 10

3-(1-Oxo-4-aminoisoindolin-1-yl)-3-methylpiperidine-2,6-dione 3-(1-Oxo-4-nitroisoindolin-1-yl)-3-methylpiperidine-2,6-dione (1.0 g, 3.3 mmol) was dissolved in methanol (500 mL) with gentle heat and allowed to cool to room temperature. To this solution was added 10% Pd/C (0.3 g) under nitrogen. The mixture was hydrogenated in a Parr apparatus at 50 psi of hydrogen for 4 hours. The mixture was filtered through celite and the celite washed with methanol (50 mL). The filtrate was concentrated in vacuo to an off white solid. The solid was slurried in methylene chloride (20 mL) for 30 min. The slurry was then filtered and the solid dried (60° C., <1 mm) to afford 0.54 g (60%) of 3-(1-oxo-4-aminoisoindolin-1-yl)-3-methylpiperidine-2,6-dione as a white solid: mp 268-270° C.; $^1$H NMR (DMSO-d$_6$) δ 10.85 (s, 1H), 7.19-7.13 (t, J=7.63 Hz, 1H), 6.83-6.76 (m, 2H), 5.44 (s, 2H), 4.41(s, 2H), 2.71-2.49 (m, 3H), 1.9-1.8 (m, 1H), 1.67 (s, 3H); $^{13}$C NMR (DMSO-d$_6$) δ 173.7, 172.49, 168.0, 143.5, 132.88, 128.78, 125.62, 116.12, 109.92, 56.98, 46.22, 29.04, 27.77, 20.82; HPLC, Waters Nova-Pak/C18 column, 4 micron, 1 mL/min, 240 nm, 20/80 CH$_3$CN/0.1% H$_3$PO$_4$(aq), 1.5 min (99.6%); Anal. Calcd for C$_{14}$H$_{15}$N$_3$O$_3$: C, 61.53; H, 5.53; N, 15.38. Found: C, 58.99; H, 5.48; N, 14.29.

From 3-(1-oxo-4-nitroisoindolin-1-yl)-3-ethylpiperidine-2,6-dione and 3-(1-oxo-4-nitroisoindolin-1-yl)-3-propylpiperidine-2,6-dione there is similarly obtained 3-(1-oxo-4-aminoisoindolin-1-yl)-3-ethylpiperidine-2,6-dione and 3-(1-oxo-4-aminoisoindolin-1-yl)-3-propylpiperidine-2,6-dione, respectively.

EXAMPLE 11

Tablets, each containing 50 mg of 1-oxo-2-(2,6-dioxo-3-methylpiperidin-3-yl)-4,5,6,7-tetrafluoroisoindoline, can be prepared in the following manner:

| Constituents (for 1000 tablets) | |
| --- | --- |
| 1-oxo-2-(2,6-dioxo-3-methylpiperidin-3-yl)-4,5,6,7-tetrafluoroisoindoline | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 12

Tablets, each containing 100 mg of 1-oxo-2-(2,6-dioxopiperidin-3-yl)$_4$-aminoisoindoline, can be prepared in the following manner:

| Constituents (for 1000 tablets) | |
| --- | --- |
| 1-oxo-2-(2,6-dioxopiperidin-3-yl)-4-aminoisoindoline | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 13

Tablets for chewing, each containing 75 mg of 2-(2,6-dioxo-3-methylpiperidin-3-yl)-4-aminophthalimide, can be prepared in the following manner:

| Composition (for 1000 tablets) | |
|---|---|
| 2-(2,6-dioxo-3-methylpiperidin-3-yl)-4-aminophthalimide | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 2-(2,6-Dioxo-3-methylpiperidin-3-yl)-4-aminophthalimide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 14

Tablets, each containing 10 mg of 2-(2,6-dioxoethylpiperidin-3-yl)-4-aminophthalimide, can be prepared in the following manner:

| Composition (for 1000 tablets) | |
|---|---|
| 2-(2,6-dioxoethylpiperidin-3-yl)-4-aminophthalimide | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 15

Gelatin dry-filled capsules, each containing 100 mg of 1-oxo-2-(2,6-dioxo-3-methylpiperidin-3-yl)-4,5,6,7-tetrafluoroisoindoline, can be prepared in the following manner:

| Composition (for 1000 capsules) | |
|---|---|
| 1-oxo-2-(2,6-dioxo-3-methylpiperidin-3-yl)-4,5,6,7-tetrafluoroisoindoline | 100.0 g |
| microcrystalline cellulose | 30.0 g |
| sodium lauryl sulfate | 2.0 g |
| magnesium stearate | 8.0 g |

The sodium lauryl sulfate is sieved into the 1-oxo-2-(2,6-dioxo-3-methylpiperidin-3-yl)-4,5,6,7-tetrafluoroisoindoline through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm mesh width and, after mixing for a further 3 minutes, the mixture is introduced in portions of 140 mg each into size 0 (elongated) gelatin dry-fill capsules.

EXAMPLE 16

A 0.2% injection or infusion solution can be prepared, for example, in the following manner:

| 1-oxo-2-(2,6-dioxo-3-methylpiperidin-3-yl)-4,5,6,7-tetrafluoroisoindoline | 5.0 g |
|---|---|
| sodium chloride | 22.5 g |
| phosphate buffer pH 7.4 | 300.0 g |
| demineralized water | to 2500.0 mL |

1-Oxo-2-(2,6-dioxo-3-methylpiperidin-3-yl)-4,5,6,7-tetrafluoroisoindoline is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

What is claimed is:

1. A compound of formula (I), or a salt or an optical isomer thereof:

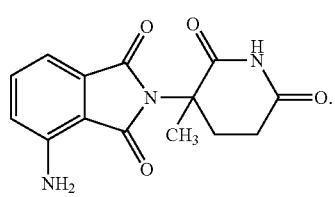

(I)

2. The compound of claim 1 having an optical purity of >95%.

3. An optical isomer of claim 1, which is (R)-3-(3-aminophthalimido)-3-methylpiperidine-2,6-dione or (S)-3-(3-aminophthalimido)-3-methylpiperidine-2,6-dione.

4. A pharmaceutical composition comprising a therapeutically effective amount of the compound, the salt or the optical isomer of claim 1, and a pharmaceutically acceptable carrier, diluent or excipient.

5. The pharmaceutical composition of claim 4 wherein the therapeutically effective amount is for reducing levels of TNFα, or treating inflammatory, autoimmune, oncogenic or cancerous disease in a mammal.

6. The pharmaceutical composition of claim 4, wherein said composition is in the form of a tablet, a capsule, a lozenge, a cachet, a solution, a suspension, an emulsion, a powder, an aerosol, a spray, a suppository, a tampon, a pessary, a pastille, an ointment, a cream, a paste, a foam or a gel.

7. The pharmaceutical composition of claim 4, wherein said composition is suitable for oral, parenteral, topical, rectal, sublingual, buccal, vaginal, transdermal, or basal administration.

8. The pharmaceutical composition of claim 6, wherein said composition is in the form of a tablet.

9. The pharmaceutical composition of claim 6, wherein said composition is in the form of a capsule.

* * * * *